United States Patent [19]

Aziz et al.

[11] Patent Number: 5,227,382
[45] Date of Patent: Jul. 13, 1993

[54] PHARMACEUTICALS

[75] Inventors: Abdel B. M. S. A. Aziz; Esmat S. Mohamed, both of Cairo, Egypt

[73] Assignee: Bio-Physio Pharmaceutical Research & Development Company Ltd., Valletta, Malta

[21] Appl. No.: 804,667

[22] Filed: Dec. 10, 1991

[30] Foreign Application Priority Data

Dec. 10, 1990 [EP] European Pat. Off. ......... 90313368.4

[51] Int. Cl.$^5$ ............................................. A61K 31/505
[52] U.S. Cl. ..................................... 514/267; 514/912
[58] Field of Search ................................ 514/267, 912

[56] References Cited

FOREIGN PATENT DOCUMENTS 0296848 12/1988 European Pat. Off. .

OTHER PUBLICATIONS

Ali et al., "Synthesis and Reactions of 2,3-Dihydro-5-Aryl-5H,6H-Thiazolo[3,2-b]-2,4-Diaza-Fluorene-3,6-Diones of Potential Biological Activities," Phosphorus and Sulfur, 1988, vol. 39, pp. 211–216, printed in the United Kingdom.
Chemical Abstracts, vol. 70, 1969, pp. 377–378, abstract No. 4016c, Columbus, Ohio, F. Grunsbergs et al.: "2,4-Diazafluorene-3,9-diones from 2-benzylidene-1,-3-indandiones," & Latv. PSR Zinat. Akad. Vestis, Kim. Ser. 1968, (3) 324-7.
Chemical Abstract, 111:23468h (1988)-Mohamed et al.

*Primary Examiner*—Frederick E. Waddell
*Assistant Examiner*—Zohreh A. Fay
*Attorney, Agent, or Firm*—Nixon & Vanderhye

[57] ABSTRACT

Compounds of the formula:

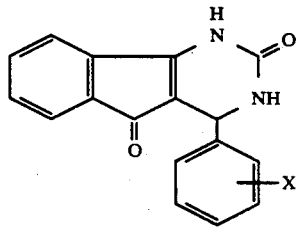

wherein X is H or halogen or a $NO_2$, $C_1$-$C_6$ alkyl or alkoxy group, are useful to treat cataract of the eye. The compounds are prepared by ring closure of the compound of formula:

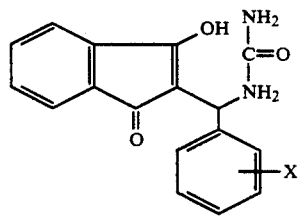

14 Claims, 3 Drawing Sheets

Fig. 3
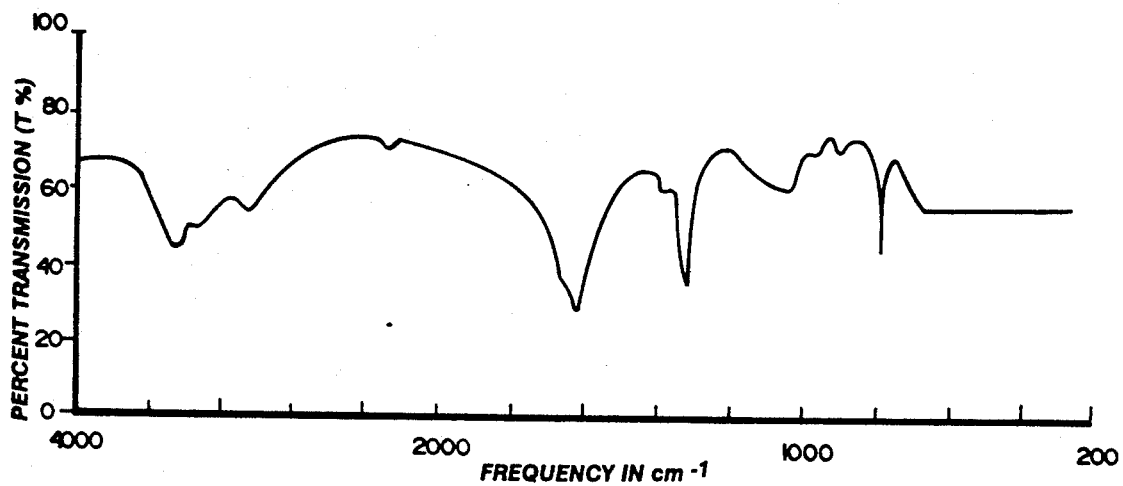
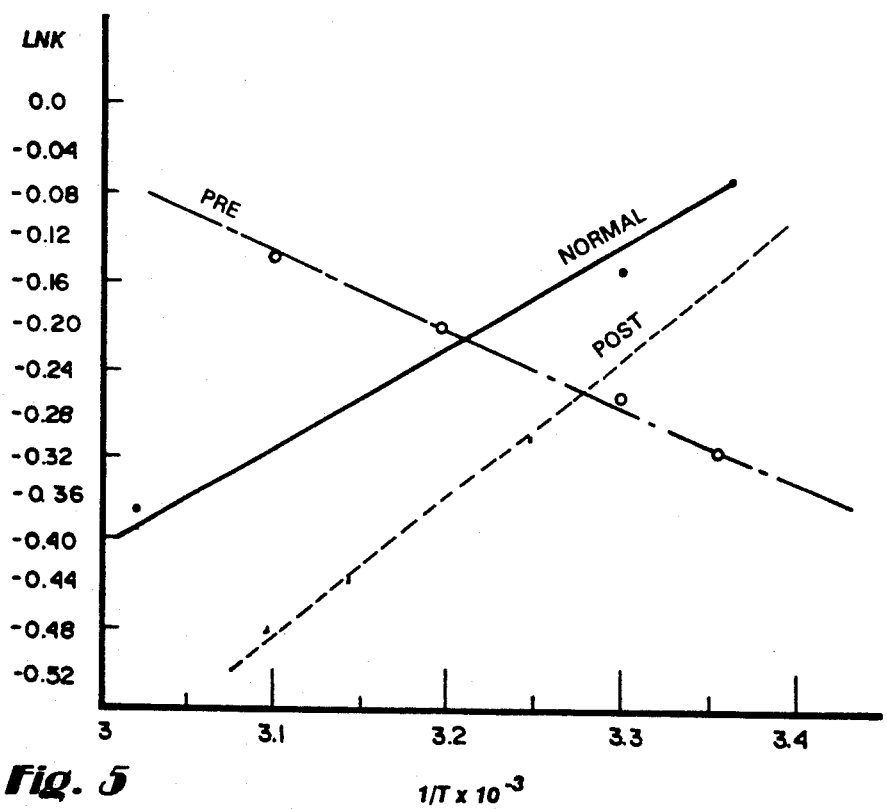
Fig. 5

PHARMACEUTICALS

This invention relates to new chemical compounds, useful in the treatment of cataract of the eye, to their preparation and use and to compositions containing them.

Cataract is the opacification of the lens of the eye which is normally clear. This opacification is caused by the denaturing of the lens proteins which is accompanied by great diminution of vision until it is reduced to hand movement only. The denaturing can be caused by various factors including senility, diabetes, metallic poisoning, exposure to irradiation etc., but the result is always the same, opacification of the lens proteins. These are $\alpha$, $\beta$ and $\gamma$ crystallines.

The fate a cataractous lens is usually as follows:

1. It may become hypermature with exfoliation of the lens capsule.
2. The cataract may undergo a process of spontaneous autolysis leading to clarification again of the substance of the lens by being replaced by clear fluid. This fluid may diffuse out through the capsule of the lens leading to signs of irritation of the eye.

This process of spontaneous clarification, which occurred very rarely (one in 5,000), led us to investigate the possibility of trying to imitate this process using proteolytic enzymes but this proved to be unsuccessful. When those experiments failed, we investigated other materials that might produce renaturation of lens proteins physically rather than chemically, in order to avoid the production of proteolytic degradation products such as amino acids which are an irritant to the eye.

It is known that lens protein has no fluctuating fringe and the phase transition from crystalline to a coil is a first order transition. This transition occurs during the denaturation of the protein. Denaturation, which is the destruction of higher structural levels with retention of the primary structure of the chain can be caused by many factors as previously mentioned. This transition process means the loss of the quaternary and tertiary structure forces as well as the secondary ones.

Our aim has therefore been to find new compounds which make it possible to decrease enthalpy or heat content i.e. reversible process of the above-mentioned transition steps or renaturation and which can bring about renaturing of denatured lens proteins by physical rather than chemical means.

BRIEF DESCRIPTION OF THE DRAWINGS

FIG. 3 shows the infra-red spectrum of the renatured lens protein;

FIG. 5 is a graph showing the threshold turning point of denature crystallines and denature ones (solid line=-normal, interrupted line=pre and dashed line=post).

DESCRIPTION OF THE INVENTION

Figure 1:
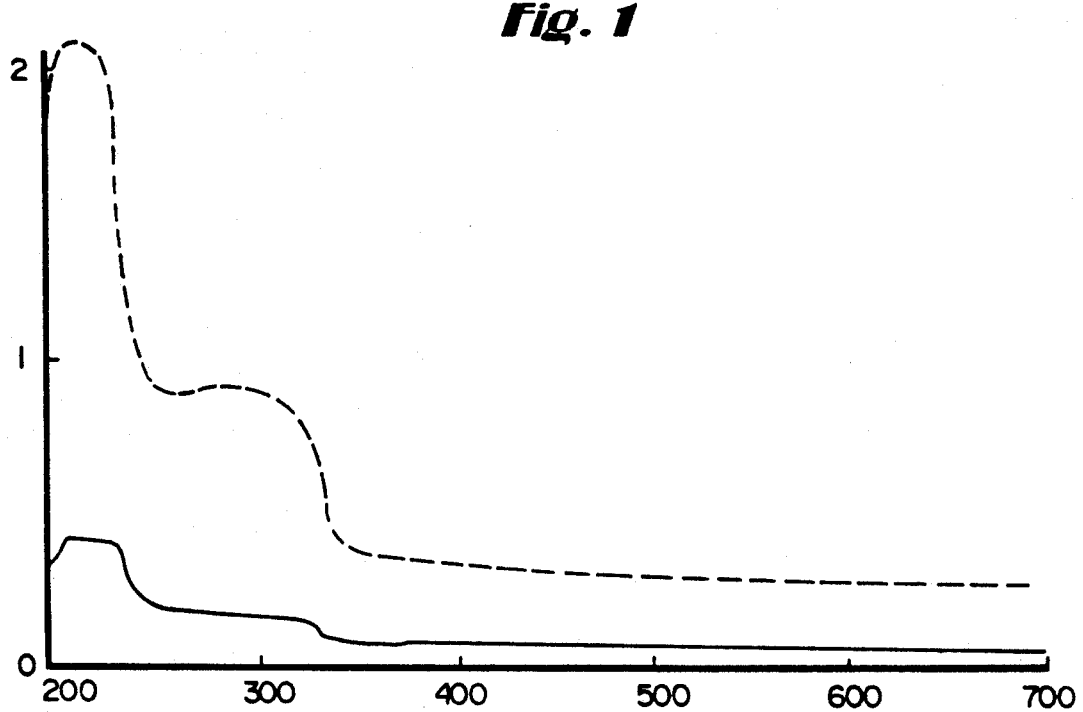
FIG. 1 is a graph showing the infra-red absorption spectrum of lens protein before and after treatment (solid line =denatured lens protein, dashed line=after renaturing)

The present invention provides new indeno-d-pyrimidone compounds of the general formula:

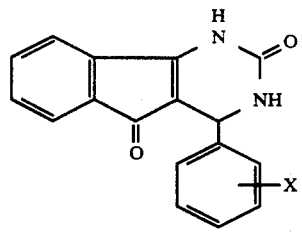

I wherein X represents H or halogen, $NO_2$ or a $C_1$-$C_6$ alkyl or alkoxy group, particularly ethyl, methoxy or ethoxy.

Preferred compounds of the invention are those where X is H, 2-chloro, 4-chloro and 4-nitro.

The compounds of the invention may be prepared by ring closure of the corresponding compound of the general formula:

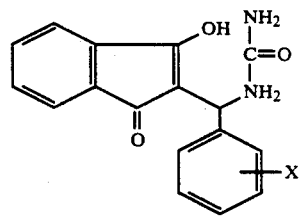

II

The ring closure can be effected by heating the compound II e.g. under reflux for 10-60 minutes.

The compound II can be prepared by reacting the compound of formula:

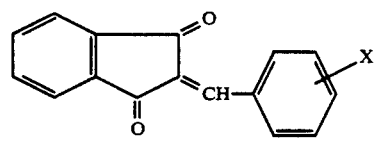

with urea, preferably in glacial acetic acid solution.

A further aspect of the present invention provides a pharmaceutical composition comprising a compound of formula I together with a pharmaceutically acceptable carrier or diluent. These compositions are normally prepared in a form suitable for direct administration to the eye and hence will be in the form of eye drops, eye ointment, eye spray etc. The proportion of active ingredients of formula I will normally be in the range 0.001-10% w/v with a preferred concentration in the range 0.01-1%.

The active ingredient of formula I will normally be formulated with a liquid carrier or diluent to form eye drops or as a water-in-oil or oil-in-water emulsion for use as an ointment. It is important that the composition shall be able to penetrate the cornea so as to transport the active compound of formula I to the region of opacified lens. Considerations of this type point to the use of diluents such as water or other aqueous solvents of pH about 7 as the liquid carrier for eye drops etc.

The aqueous formulation preferably also contains a non-ionic emulsifying agent e.g. a Tween such as Tween 20, 40, 60 or 80 in an amount of 0.01 to 1 mole % based on the compound I. Alternatively, the new compounds of the invention may be formulated in an eye ointment, an eye wash, an eye spray or in a liposome preparation.

The present invention also extends to the compounds of formula I for use in a method of treatment of the eye to bring about a reduction in lens opacity in cases of cataract and a method of treatment of a patient suffering cataract which comprises applying to the eye of such a patient an effective amount of a compound of formula I or of a pharmaceutical composition containing it.

The following Examples are given to illustrate the invention.

EXAMPLE 1

Into a refluxing solution containing 0.01 mole of

[structure: indanedione with =CHPh substituent]

in 15 ml glacial acetic acid was added 0.01 moles urea. A deep red colour immediately developed and, after 25 minutes at reflux temperature red crystals separated out. These crystals of

[structure III: indanone with NH-CHO and NH-CHPh groups]   III were separated from the reaction mixture after it had been allowed to stand for 2 hours at 20° C. and the solid recrystallised from acetic acid to give III, m.p. 225° C. in 65% yield. Similarly, the corresponding 2-chloro, 4-chloro- and 4-nitro compounds were prepared starting from the correspondingly substituted phenyl reactant. The characterisation of the compounds are set out in Table I below.

TABLE I

| Compound X | M.p. °C. | Yield | Formula m.w | Anal. % calcd./found |  |  |
|---|---|---|---|---|---|---|
|  |  |  |  | C | H | N |
| H | 225 | 65 | $C_{17}H_{12}N_2O_2$ (276.28) | 73.92 73.75 | 4.38 4.23 | 10.14 10.00 |
| 2-Cl | 240 |  | $C_{17}H_{11}ClN_2O_2$ (310.7) | 65.71 65.60 | 3.57 3.44 | 9.01 8.91 |
| 4-Cl | 300 | 60 | $C_{17}H_{11}ClN_2O_2$ (310.7) | 65.71 65.64 | 3.57 3.48 | 9.01 8.88 |
| 4-$NO_2$ | 181 | 80 | $C_{17}H_{11}N_3O_4$ (321.2) | 63.56 63.37 | 3.45 3.28 | 13.08 12.79 |

The structure of the new compounds was confirmed by physical and chemical methods. The IR spectra of compounds I showed bands at 1,725 $cm^{-1}$ and at 1,685 $cm^{-1}$, assignable to the two carbonyl groups (C=O); no absorption was seen at 1,100 $cm^{-1}$.

The IR spectra of compound 2 show absorption at 3,250 $cm^{-1}$ (NH) and at 1,650 $cm^{-1}$ and 1,700 $cm^{-1}$ (C=O); the IR spectra of compounds 3 show bands at 3,250 $cm^{-1}$ and at 3,285 $cm^{-1}$ (NH), at 1,685 $cm^{-1}$ (C=O) and a very strong band at 1,100 $cm^{-1}$ assignable to (C=S).

Findings and interpretation of in vitro and in vivo experiments:

It was found that using an aqueous solution of compound III (X=H) of Example 1 in 6M concentrations led to the transparency of mature cataractous lens protein in vitro after soaking for 5 minutes. This process occurred through reversible steps of denaturation i.e. renaturation.

This renaturation takes place through changes of the tertiary structure without any change in the primary one, i.e. rearrangement physically, according to the following 6 proofs in which a 6M aqueous solution of compound III (X=H) was used as the test solution:

1st Proof:

FIG. 1 shows the infra-red absorption spectrum of lens protein before and after treatment, and the change in the extension coefficient at 220 and 280 n.m. (FIG. 1).

Figure 2:
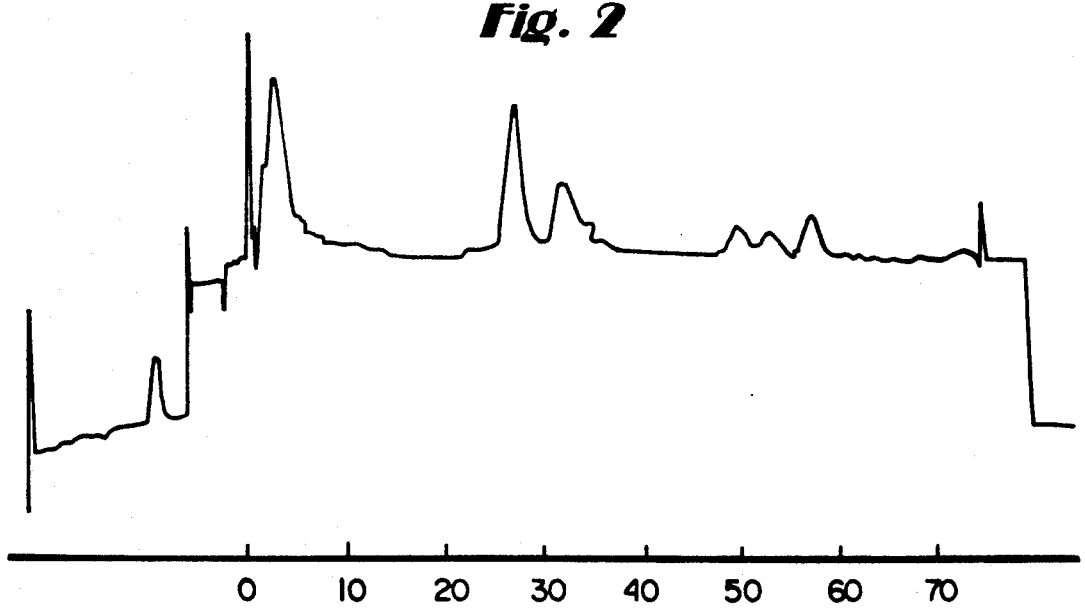
FIG. 2 is a graph showing the results of amino acid analysis on the lens proteins after renaturation and shows the absence of any free amino acids.

2nd Proof:

FIG. 2 shows the results of amino acid analysis on the lens proteins after renaturation and shows the absence of any free amino acids. This result demonstrates that renaturation of coil $\alpha$, $\beta$ and $\gamma$ crystallines occurred through a physical process, e.g. through the electrostatic forces, hydrogen bonds, and hydrophilic, hydrophobic interaction.

3rd Proof:

FIG. 3 shows the infra-red spectrum of the renatured lens protein and indicates the three types of crystalline $\alpha$, $\beta$ and $\gamma$. It is important to mention that these three types of crystallines have the same fingerprint as the native protein.

Figure 4:
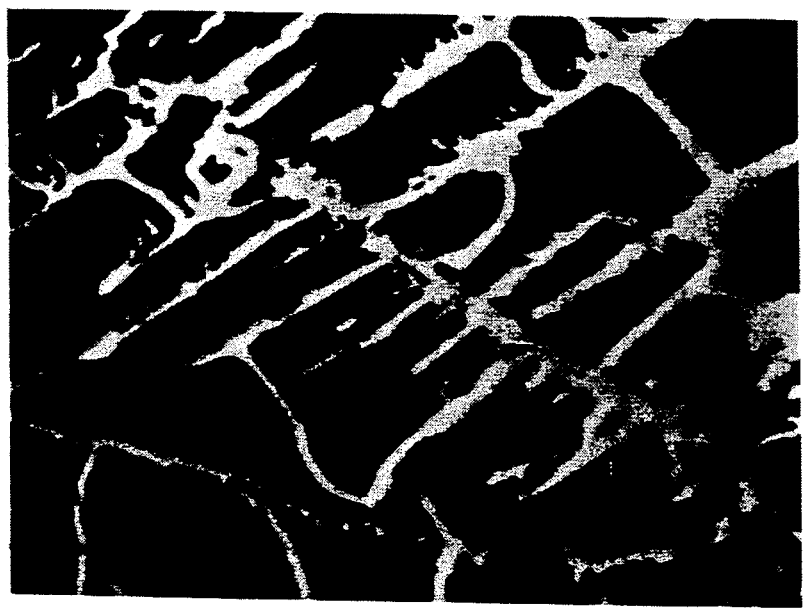
FIG. 4 shows the scanning electron microscopy spectrum of the renatured lens protein which indicates the absence of coil protein.

4th Proof:

FIG. 4 shows the scanning electron microscopy spectrum of the renatured lens protein which indicates the absence of coil protein. Moreover it gives a line of evidence about the lattice configuration of the native lens protein.

5th Proof:

This is the bioenergetics which furnish information of native crystalline (obtained post mortem) denature and after renaturation with the test solution.

$$\text{Native crystalline} \underset{**(-\Delta G, \Delta H, \Delta S)}{\overset{*(+\Delta G, \Delta H, \Delta S)}{\rightleftarrows}} \text{denature ones}$$

*Denaturation process
**Renaturation

Constant of this process was calculated from Arrhenius equation as follows:

$K = (A_{280}/1 - A_{280})$.

$G^o = {}^-RT \ln k$ joule/mole hence R—gas constant

T—absolute temperature

It should be noted that $\Delta H$ and $\Delta S$ have been computed from the slope of plots lnk vrs 1/T. FIG. 5 shows the threshold turning point of denature crystallines and renature ones. This means that both $\Delta H$ (heat content) and entropy ($\Delta S$) or molecular disorder are decreased and turned to negative signs after being high and positive in the denatured ones. The randomicity or entropy of renatured crystallines approached in its value and direction the native ones.

6th Proof:

The refractive index of renatured lens protein approached that of the native protein.

Thus, one may conclude that the compounds of the invention gave the denatured lens protein crystallines the mobility and the internal flexibility to gain the forces of the tertiary structure after being in the coil form. After renaturation, the resulting lens protein crystallines possessed the same stability and the function of the native material.

Another advantage of the compounds of the invention, besides the above mentioned, is that it is safe to use in vivo as shown in animal experiments on dogs and rabbits. These experiments lead to the transparency of the induced irradiated cataract, after applying the aqueous eye drops containing 0.05 ml Tween 60 per mole of compound III three times daily for a period up to 7 days. Transparency of the lens occurred without development of any side effects such as irritation or allergic reaction.

The application of formulations of the invention on cataractous human lens protein also gave similar beneficial results as mentioned above for the animals. In these tests the transparency of cataractous lens protein was demonstrated by the clinical improvement of vision, red reflex test and the comparison of ultrasonography pictures taken before and after treatment.

Direct photography of the anterior segment of the eye also showed the difference between the configuration of the lens before and after treatment.

We claim:

1. A pharmaceutical composition for topical application to the eye for the treatment of cataract comprising a compound of the formula I:

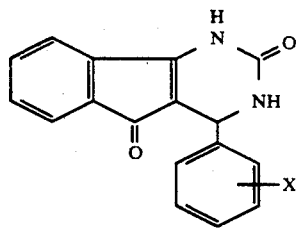

wherein X is H or halogen or a $NO_2$, $C_{1-6}$ alkyl or alkoxy group together with a pharmaceutically acceptable carrier or diluent.

2. The pharmaceutical composition according to claim 1 wherein in the compound of formula (I) X is H, 2-chloro, 4-chloro or 4-nitro.

3. The pharmaceutical composition according to claim 1 which contains from 0.1% to 1% w/v of the compound of formula (I).

4. The pharmaceutical composition according to claim 1 which also comprises a non-ionic emulsifying agent.

5. The pharmaceutical composition according to claim 1 in the form of eye drops or an eye ointment.

6. The pharmaceutical composition according to claim 1 which contains from 0.001% to 10% w/v of the compound of formula I.

7. A method of treating a patient suffering cataract which comprises applying to the eye of such a patient an effective amount of a compound of formula (I):

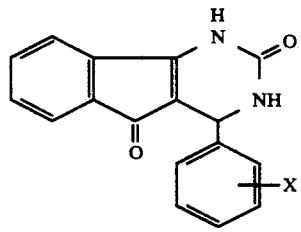

wherein the group X is halogen or a $NO_2$, $C_{1-6}$ alkyl or alkoxy group.

8. The method according to claim 7 wherein in the compound of formula (I) the group X is hydrogen, 2-chloro, 4-chloro or 4-nitro.

9. A method of treating a patient suffering cataract which comprises applying to the eye of such a patient a composition comprising together with a pharmaceutically acceptable carrier or diluent an effective amount of a compound of formula (I):

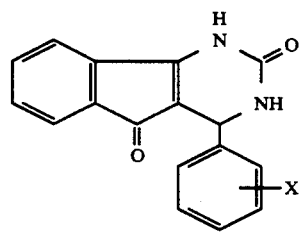

wherein the group X is halogen or a $NO_2$, $C_{1-6}$ alkyl or alkoxy group.

10. The method according to claim 9 wherein X is hydrogen, 2-chloro, 4-chloro or 4-nitro.

11. The method according to claim 9 wherein the composition comprises from 0.001% to 10% w/v of the compound of the compound of the formula (I).

12. The method according to claim 11 wherein the composition comprises from 0.1% to 1% w/v of the compound of formula (I).

13. The method according to claim 9 wherein the composition also comprises a non-ionic emulsifying agent.

14. The method according to claim 9 wherein the composition is in the form of eye drops or an eye ointment.

* * * * *